(12) United States Patent
Phipps

(10) Patent No.: US 9,433,508 B2
(45) Date of Patent: Sep. 6, 2016

(54) SHOULDER IMPLANT SYSTEM

(71) Applicant: Zimmer, Inc., Warsaw, IN (US)

(72) Inventor: James P. Phipps, South Whitley, IN (US)

(73) Assignee: Zimmer, Inc., Warsaw, IN (US)

( * ) Notice: Subject to any disclaimer, the term of this patent is extended or adjusted under 35 U.S.C. 154(b) by 87 days.

(21) Appl. No.: 14/030,484

(22) Filed: Sep. 18, 2013

(65) Prior Publication Data

US 2014/0088722 A1 Mar. 27, 2014

Related U.S. Application Data

(60) Provisional application No. 61/704,134, filed on Sep. 21, 2012.

(51) Int. Cl.
*A61F 2/40* (2006.01)
*A61F 2/46* (2006.01)
*A61F 2/30* (2006.01)

(52) U.S. Cl.
CPC ........... *A61F 2/4081* (2013.01); *A61F 2/4014* (2013.01); *A61F 2/4059* (2013.01); *A61F 2/4612* (2013.01); *A61F 2002/30332* (2013.01); *A61F 2002/30616* (2013.01); *A61F 2002/4018* (2013.01); *A61F 2002/4029* (2013.01); *A61F 2002/4037* (2013.01); *A61F 2002/4044* (2013.01); *A61F 2002/4062* (2013.01)

(58) Field of Classification Search
CPC .............. A61F 2/4014; A61F 2/4059; A61F 2002/4051; A61F 2002/4062; A61F 2002/4018; A61F 2002/4037
USPC ....................................... 623/19.13
See application file for complete search history.

(56) References Cited

U.S. PATENT DOCUMENTS 5,282,861 A 2/1994 Kaplan
6,986,790 B2 * 1/2006 Ball et al. .................. 623/19.11

(Continued)

FOREIGN PATENT DOCUMENTS

EP 2324800 A1 5/2011
EP 2897558 A1 7/2015
WO WO-2014047155 A1 3/2014

OTHER PUBLICATIONS

"International Application Serial No. PCT/US2013/060371, International Preliminary Report on Patentability mailed Apr. 2, 2015", 8 pgs.

(Continued)

*Primary Examiner* — Javier Blanco
(74) *Attorney, Agent, or Firm* — Schwegman Lundberg & Woessner, P.A.

(57) ABSTRACT

Art apparatus can include a humeral stem. A glenosphere can be configured to be mountable to the humeral stem. The glenosphere can be adapted to operate with a complementary glenoid component. The humeral stem can include a removable taper member on a side of the humeral stem facing the glenosphere. The taper member can be configured to mount the glenosphere to the humeral stem.

3 Claims, 4 Drawing Sheets

(56) References Cited

U.S. PATENT DOCUMENTS

| | | |
|---|---|---|
| 7,959,680 B2 | 6/2011 | Stone et al. |
| 8,070,820 B2 | 12/2011 | Winslow et al. |
| 2004/0002765 A1 | 1/2004 | Maroney et al. |
| 2004/0220674 A1* | 11/2004 | Pria .......... A61F 2/40 623/19.12 |
| 2005/0113931 A1 | 5/2005 | Horber |
| 2005/0143829 A1* | 6/2005 | Ondrla et al. ........ 623/19.14 |
| 2005/0251263 A1* | 11/2005 | Forrer ............ A61F 2/4014 623/19.13 |
| 2011/0118846 A1* | 5/2011 | Katrana et al. .......... 623/19.13 |

OTHER PUBLICATIONS

"International Application Serial No. PCT/US2013/060371, International Search Report mailed Nov. 4, 2013", 5 pgs.

"International Application Serial No. PCT/US2013/060371, Written Opinion mailed Nov. 4, 2013", 6 pgs.

* cited by examiner

SHOULDER IMPLANT SYSTEM

CLAIM OF PRIORITY

This application claims the benefit of U.S. Provisional Patent Application Ser. No. 61/704,134, filed on Sep. 21, 2012, the benefit of priority of which is claimed hereby, and which is incorporated by reference herein in its entirety.

FIELD

The present subject matter relates to an orthopedic system and specifically to a shoulder implant system.

BACKGROUND

In a healthy shoulder, the proximal humerus is generally ball-shaped, and articulates within a socket formed by the scapula, called the glenoid, to form the shoulder joint. Some implant systems for the total replacement of the shoulder joint generally replicate the natural anatomy of the shoulder. Such implant systems can include a humeral component having a stem that fits within the humeral canal, and an articulating head that articulates within the socket of a glenoid component implanted within the glenoid of the scapula. For example, U.S. Pat. Nos. 8,070,820 and 7,959,680 discuss shoulder implant systems.

OVERVIEW

A humeral stem and a glenosphere configured to be mountable to the humeral stem. The glenosphere can be adapted to operate with a complementary glenoid component. The humeral stem can include a removable taper member on a side of the humeral stem facing the glenosphere. The removable taper member can be configured to mount the glenosphere to the humeral stem.

The humeral stem can include an attachment sec ion configured to allow attachment and removal of the removable taper section. The attachment section can include a threaded rod configured to receive the removable taper member. The threaded rod can include an unthreaded lead-in section dimensioned to promote axial alignment of the taper member relative to the threaded rod. The glenoid component can include a surface adapted to be attached to a body. The glenoid component can include one or more stems. The taper member can include a 60 degree Morse taper region. The glenosphere can include a corresponding taper region to receive the taper member.

A glenoid surface and a humeral stem having an attachment section. A taper member can be removably attached to the attachment section of the humeral stem. A glenosphere can be mounted to the taper member, the glenosphere can be adapted to operate with the glenoid surface.

The attachment section can include a threaded rod and the taper member can include a mating threaded hole. The threaded rod can include an unthreaded lead-in section dimensioned to promote axial alignment of the taper member relative to the threaded rod. The glenoid surface can be located on a base plate including a stem extending from a first side of the base plate. The taper member can include a 60 degree Morse taper region. The glenosphere can include a corresponding taper region to receive the taper member.

A method can include attaching a removable taper member to a humeral stem and mounting a glenosphere to the taper member.

Attaching can include threading the taper member to the humeral stem. Attaching can include placing the taper member over an unthreaded lead-in section of a threaded rod on the humeral stem to axially align the taper member to the threaded rod before the threads of the threaded rod meet the threads of the taper member. The method can further include removing the taper member and attaching a second, different taper member to the humeral stem. The taper member can include a 60 degree Morse taper region. The glenosphere can include a corresponding taper region to receive the taper member.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
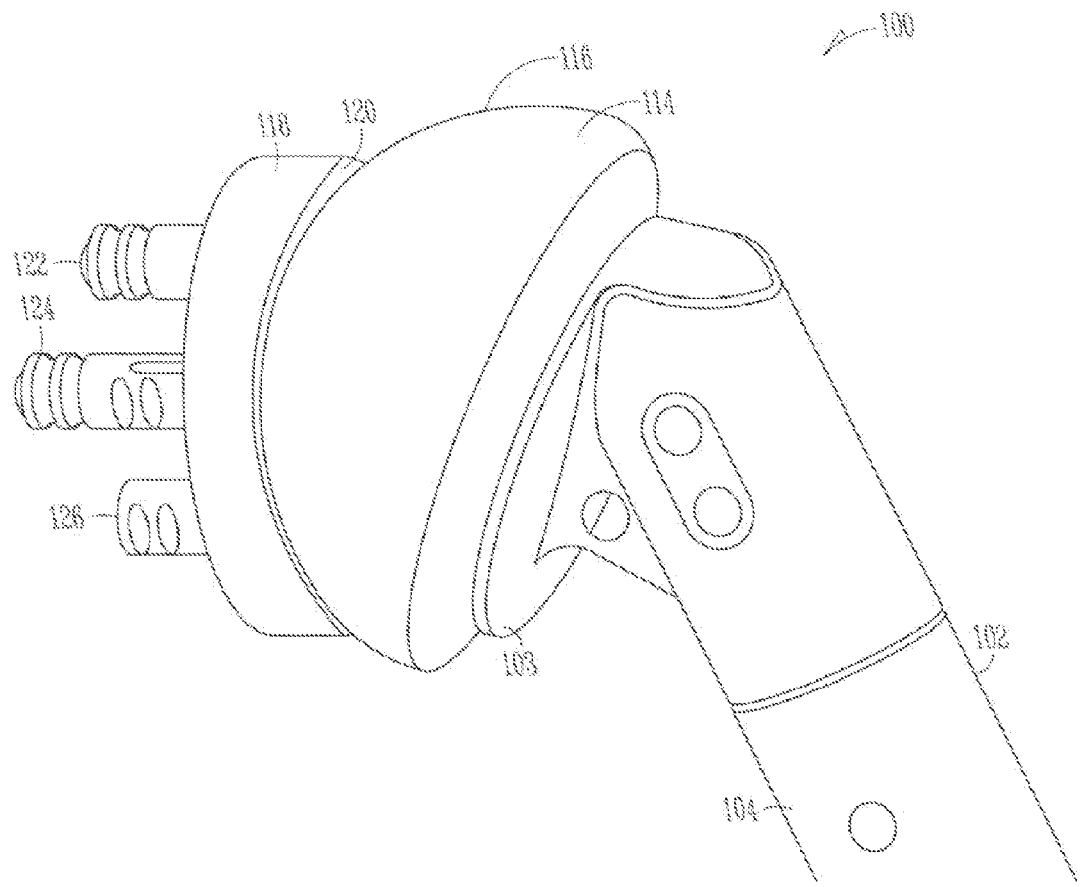
FIG. 1 shows an implant system for a shoulder arthroplasty.

FIG. 1 shows a shoulder implant system 100 for a shoulder arthroplasty, in accordance with one embodiment. The shoulder implant system 100 can include a humeral stem 102 that can be sized or shaped or otherwise adapted to be fitted within a prepared proximal end canal of a humerus, a glenosphere 114 mounted to an end of the humeral stem 102, and a glenoid component 118 that can be sized or shaped or otherwise configured to be mounted to a prepared surface of a patient's glenoid. The glenosphere 114 can include a convex articulating outer surface 116 shaped to articulate with a complementary concave articulating glenoid surface 120 of the glenoid component 118, such as to replicate the movement of the natural shoulder joint.

The humeral stem 102 can include a stem portion 104 and an upper glenosphere attachment portion 103. The glenoid component 118 can include a back surface adapted to be mounted to a patient's glenoid cavity. For example, the glenoid component 118 can include one or more attachment stems 122, 124, 126 extending from the back surface. An outer porous surface on the back surface can be adapted to promote bone growth. For example, the back surface can include a porous metallic surface.

For example, the back surface can include a highly porous biomaterial useful as a bone substitute and/or cell and tissue receptive material. An example of such a material can be produced using Trabecular Metal® technology generally available from Zimmer, Inc., of Warsaw, Ind. Trabecular Metal® is a trademark of Zimmer Technology, Inc. Such a material can be formed from a reticulated vitreous carbon foam substrate, which can be infiltrated and coated with a biocompatible metal, such as tantalum, etc., such as using a chemical vapor deposition ("CVD") process, such as in the manner disclosed in detail in U.S. Pat. No. 5,282,861, the disclosure of which is incorporated herein by reference. One or more other metals such as niobium, titanium, or one or more alloys of tantalum and niobium with each other or with one or more other metals can also be used.

Figure 2:
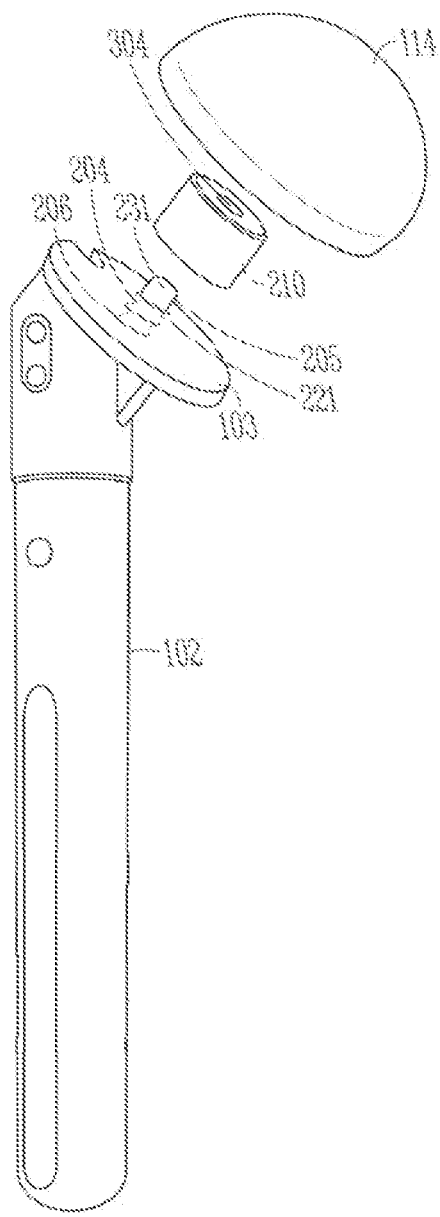
FIG. 2 shows an exploded perspective view of the implant system of FIG. 1.
Figure 3:
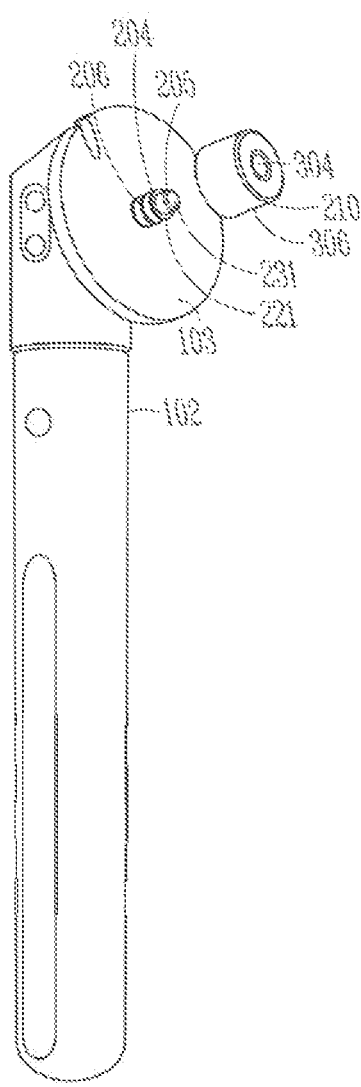
FIG. 3 shows a perspective view of the humeral stem of the implant system of FIG. 1.

FIG. 2 shows an exploded perspective view of the implant system 100, and FIG. 3 shows a perspective view of the humeral stem 102.

The glenosphere attachment portion 103 can include a taper attachment section 204 that can extend from the surface of the attachment portion 103. The taper attachment section 204 can be adapted to receive the removal taper member 210 and to allow a user to remove the removable taper member 210 without damaging the attachment portion 103. The taper attachment section 204 can include a threaded rod 221 such as to receive the removable taper member 210. The threaded rod 221 can extend from the surface of the glenosphere attachment portion 103 and can include a lower threaded section 206, a rounded top 231, and an unthreaded lead-in section 205. The unthreaded lead-in section 205 can have a height dimensioned to promote axial alignment of the removable taper member 210 relative to the threaded rod 221 when the taper member 210 is mounted to the glenosphere attachment portion 103. The unthreaded lead-in section 205 and/or the rounded top 231 can help inhibit thread misalignment between the two members and can make it easier for a user to install the taper member 210 to the threaded rod 221. The threaded rod 221 can include a ¼-20 threaded rod, such as can protrude from the center axis of the glenosphere attachment portion 103.

The taper member 210 can be generally cylindrical with a tapered outer surface shape 306. The taper member 302 can include a threaded hole 304 that can be configured to removably receive the threaded rod 221 such as discussed herein. This allows taper member 210 to be removed from the glenosphere attachment portion 103 and a similar or different taper member can be mounted to the glenosphere attachment portion 103 without the humeral stem 102 having to be removed from its implanted location. This removability/interchangeability of the present taper system allows a doctor to revise the taper region of the implant as needed without unnecessary complications. The taper member 210 can be configured to mount the glenosphere 114 to the glenosphere attachment portion 103. The taper member 210 can have a 60 degree Morse taper region defined by its tapered outer surface shape 306. The Morse taper region can provide a conical press-fit fixation of the taper member 302 into the corresponding taper region of the glenosphere 114, such as for providing accurate alignment and frictional fixation. Another Morse taper size can be used depending on need and requirements of the corresponding glenosphere used.

Figure 4:
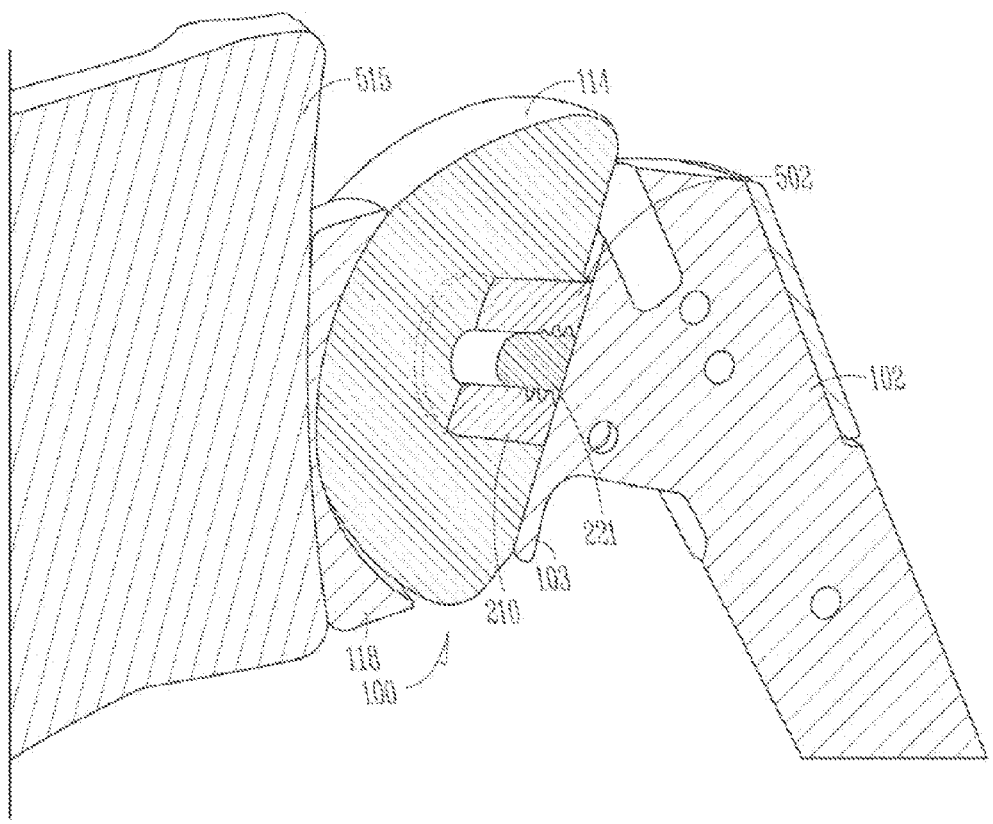
FIG. 4 shows a side view of the shoulder implant system of FIG. 1.

FIG. 4 shows a side view of the shoulder implant system 100. The system can include the humeral stem 102 fitted the glenosphere 114. The glenoid component 118 can be mounted to a prepared surface of a patient's glenoid 515. The removable taper member 210 can be fitted to the glenosphere 114. The glenosphere 114 can have a female taper region 502 and the removable taper member 210 can fit within the corresponding taper region 502. The threaded rod 221 can extend from the surface of the glenosphere attachment portion 103 and can receive the removable taper member 210.

In use, the glenoid component 118 can be implanted to the patient's glenoid 515. The taper member 210 can be screwed onto the glenosphere attachment portion 103 over the threaded rod 221. The glenosphere 114 can then be force fit over the taper member 210. If revision is needed, the glenosphere 114 can be removed from the taper member 210 and, if needed, the taper member 210 can be removed, such as by unthreading from the threaded rod 221. A similar or a different taper member can then be threaded onto the threaded rod 221. For example, if the doctor decides to use a different size glenosphere having a different size taper region 502, a matching taper member can be used. Depending on the adjustable glenosphere used, or for other considerations, the different sized taper member can be any combination of wider, thinner, tatter, or shorter than the present taper member.

Accordingly, the present system can include a humeral stem 102 with a removable/interchangeable taper member 210 such as to allow for the removal of the taper member 210 of the implant without disrupting the rest of the implant that has established bone ingrowth. For example, sometimes during a revision surgery, the entire humeral stem component from a total shoulder arthroplasty procedure must be removed to provide an undisturbed taper surface for the implant. In the present system, taper member 210 can be exchanged for a different type of taper for use with a different glenosphere to be installed in the patient.

The removable taper member 210 is user-removable and can allow a surgeon to replace only the tapered section of the humeral stem implant, such as if this were to become compromised by a failed attempt to seat the glenosphere during the surgery. The removable taper member 210 can also be helpful to a surgeon performing a revision procedure because the doctor would be able to remove the old taper and insert a fresh taper component without disturbing the rest of the implant, which may have already established bone ingrowth.

Moreover, using a removable taper member 210 can allow for a shorter or taller taper member to be used, which can allow the doctor to control the axial distance of the glenosphere 114. Having an axial distance adjustable glenosphere 114 can allow surgeons to custom build each implant to the particular patient anatomy for tightening the joint space, for example. For example, a surgeon can choose a shorter or longer taper member 210, such as depending on the chosen glenosphere and the patient's anatomy, to provide the desired fit. Also, choosing a different height for the taper member 210 can provide the ability to tension the joint from the humeral side of the shoulder. It is believed that this can help provide less scapular notching from the humeral component than is seen with current competitive systems on the market, since the humeral stem 102 can be moved away from the scapula. The present interchangeable taper member 210 would allow surgeons more adjustability in joint anatomy, which may lead into orthopedic avenues in total shoulder arthroplasty that have not yet been uncovered.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. A shoulder prosthesis comprising:
   a glenoid component configured to be mounted to a glenoid, the glenoid component located on a base plate;
   a humeral stem including a stem portion and a glenosphere attachment portion, the glenosphere attachment portion having a threaded attachment post integrally formed therewith and extending away from a surface of the glenosphere attachment portion, the threads of the attachment rod being exposed;
   a removable taper member removably attached to the attachment post of the humeral stem, the taper member being generally cylindrical with a tapered outer surface, the taper member adapted to being mounted over the threads of the attachment post and un-mounted from the attachment post; and
   a glenosphere mounted to the taper member, the glenosphere including a corresponding taper region comprising a shape and length complementary to a shape and length of the taper member, said corresponding taper region receiving the taper member,
   wherein the removable taper member is configured to mount the glenosphere to the attachment portion of the humeral stem, and wherein the glenosphere is adapted to operate with the glenoid component,
   wherein the threaded attachment post is defined by a threaded rod and the taper member includes a mating threaded hole extending therethrough, the threaded hole engaging the threads of the threaded rod,
   wherein the threaded rod further includes an unthreaded lead-in section dimensioned to promote axial alignment of the taper member relative to the threaded rod.

2. The shoulder prosthesis of claim 1, wherein the base plate includes a stem extending from a first side of the base plate.

3. The shoulder prosthesis of claim 1, wherein the taper member includes a 60 degree Morse taper region.

\* \* \* \* \*